United States Patent
Clarke et al.

(10) Patent No.: US 10,202,847 B2
(45) Date of Patent: *Feb. 12, 2019

(54) USE OF METAMATERIAL TO ENHANCE MEASUREMENT OF DIELECTRIC PROPERTIES OF A FLUID

(71) Applicant: SCHLUMBERGER TECHNOLOGY CORPORATION, Sugar Land, TX (US)

(72) Inventors: Andrew Clarke, Cambridge (GB); Cheng-Gang Xie, Singapore (SG); Christopher Lenn, Kuala Lumpur (MY)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/421,920

(22) PCT Filed: Aug. 14, 2013

(86) PCT No.: PCT/IB2013/056644
§ 371 (c)(1),
(2) Date: Feb. 16, 2015

(87) PCT Pub. No.: WO2014/027322
PCT Pub. Date: Feb. 20, 2014

(65) Prior Publication Data
US 2015/0218941 A1    Aug. 6, 2015

Related U.S. Application Data

(60) Provisional application No. 61/684,116, filed on Aug. 16, 2012.

(51) Int. Cl.
*E21B 49/00* (2006.01)
*E21B 49/08* (2006.01)
(Continued)

(52) U.S. Cl.
CPC .............. *E21B 49/08* (2013.01); *E21B 47/10* (2013.01); *E21B 49/00* (2013.01); *G01F 1/56* (2013.01);
(Continued)

(58) Field of Classification Search
CPC ...... G01N 24/08; G01N 24/082; E21B 49/00; E21B 49/08
(Continued)

(56) References Cited

U.S. PATENT DOCUMENTS 3,286,163 A  *  11/1966  Holser
4,739,272 A  *   4/1988  Griffin ..................... G01V 3/28
                                                    324/339
(Continued)

FOREIGN PATENT DOCUMENTS

EP    1860458 A1    11/2007
EP    2015109 A1     1/2009
(Continued)

*Primary Examiner* — Walter L Lindsay, Jr.
*Assistant Examiner* — Milton Gonzalez

(57) ABSTRACT

Systems, tools, and methods for enhancing a measurement of a fluid in a borehole, pipe, conduit and/or the like involve an electromagnetic measurement tool that includes a transmitting antenna configured to transmit electromagnetic energy, a receiving antenna configured to receive the electromagnetic energy, and a metamaterial element comprising a negative refractive index. The metamaterial element may focus the electromagnetic energy. The electromagnetic system may comprise one or more antennas that are disposed adjacent to or in contact with the fluid, electromagnetic energy may be transmitted via the transmitting antenna, and
(Continued)

the electromagnetic energy may be received with the receiving antenna to measure a property of the fluid.

34 Claims, 6 Drawing Sheets

(51) Int. Cl.
    *G01F 1/56*       (2006.01)
    *G01N 24/08*     (2006.01)
    *G01N 27/02*     (2006.01)
    *E21B 47/10*     (2012.01)
    *H01Q 15/00*     (2006.01)
    *H01Q 19/06*     (2006.01)
    *G01V 3/30*      (2006.01)

(52) U.S. Cl.
    CPC ............ *G01N 24/08* (2013.01); *G01N 27/02* (2013.01); *H01Q 15/0086* (2013.01); *H01Q 19/062* (2013.01); *G01V 3/30* (2013.01)

(58) Field of Classification Search
    USPC ........................................ 324/303, 323, 324
    See application file for complete search history.

(56) References Cited

U.S. PATENT DOCUMENTS

| | | | |
|---|---|---|---|
| 4,780,678 A * | 10/1988 | Kleinberg | |
| 5,210,406 A | 5/1993 | Beran et al. | |
| 5,485,743 A | 1/1996 | Taherian et al. | |
| 6,100,696 A * | 8/2000 | Sinclair | |
| 6,831,470 B2 | 12/2004 | Xie et al. | |
| 6,915,707 B2 | 7/2005 | Nyfors et al. | |
| 7,624,652 B2 | 12/2009 | Wee et al. | |
| 7,712,380 B2 | 5/2010 | Xie | |
| 7,908,930 B2 | 3/2011 | Xie et al. | |
| 8,159,223 B2 | 4/2012 | Luekeke et al. | |
| 8,224,588 B2 | 7/2012 | Wee | |
| 2003/0137301 A1 | 7/2003 | Thompson et al. | |
| 2003/0189511 A1 | 10/2003 | Lasky et al. | |
| 2006/0028385 A1 | 2/2006 | Davis et al. | |
| 2007/0171536 A1 * | 7/2007 | Tsukagoshi | |
| 2008/0165079 A1 * | 7/2008 | Smith | |
| 2008/0252293 A1 | 10/2008 | Lagae et al. | |
| 2009/0253227 A1 * | 10/2009 | Defries | |
| 2010/0025112 A1 * | 2/2010 | Sroka | |
| 2010/0033389 A1 * | 2/2010 | Yonak | |
| 2010/0079354 A1 * | 4/2010 | Lam | |
| 2011/0267074 A1 | 11/2011 | Xie et al. | |
| 2014/0298900 A1 | 10/2014 | Clarke | |

FOREIGN PATENT DOCUMENTS

| | | |
|---|---|---|
| GB | 2359435 B | 5/2002 |
| WO | 2009/143186 A1 | 11/2009 |
| WO | 2012094162 A2 | 7/2012 |
| WO | 2013/072844 A1 | 5/2013 |

* cited by examiner

USE OF METAMATERIAL TO ENHANCE MEASUREMENT OF DIELECTRIC PROPERTIES OF A FLUID

BACKGROUND

The present invention relates generally to methods and systems for investigating the properties of fluids using electromagnetic energy, and more particularly but not by way of limitation to investigating methods and systems for measuring one or more properties of wellbore fluids, properties of multiphase flows, properties of production fluids, properties of fluid flows in pipelines/conduits, properties of fluids in earth formation and/or the like. Merely by way of example, the described methods and systems may be used to enhance a penetration of electromagnetic energy transmitted within a material to enhance and investigation depth, and in some examples the enhanced investigation may be used in the wellbore to enhance the measurement of the one or more properties of the wellbore and/or fluids flowing in/out of the wellbore.

Various tools and devices are currently used within wellbores and pipelines/conduits to measure properties of fluids flowing therein. Determining flow properties of multiphase mixtures flowing in the wellbores and pipelines/conduits—such as flow velocity, percentages/ratios of the different phases, volume flow rate of a phase and/or the like—may be used to determine an amount of a phase, such as an oil phase, a water phase, a gas phase, a solids phase being carried in the wellbore/pipeline/conduit or contained in earth formation etc., identify presence/quantities of a phase at a location along the wellbore/pipeline/conduit etc. and/or the like.

Radio frequency ("RF") antennas, microwave antennas and/or the like have been used as part of multiphase flow metering systems. For example, U.S. Pat. No. 7,624,652 and U.S. Pat. No. 8,224,588 disclose the use of electromagnetic antennas, for example a plurality of electric-dipole antennas, for the measurement of phase fraction(s) of a multiphase flow and/or water conductivity. U.S. Pat. No. 6,915,707 discloses a multiphase flow sensor pipe-section with an integrated mechanical structure serving as a microwave resonator sensor for providing permittivity measurements of the multiphase flow, which measurements may be used to determine properties of the multiphase flow/phases of the multiphase flow (the mechanical structure also functions as a differential pressure element for providing flow rate measurements).

Transmission-reception electromagnetic antennas have been explored for multiphase flow phase fraction and/or water-cut measurement (see, e.g., U.S. Pat. No. 7,908,930, and U.S. Patent Pub No. 20110267074) and for tomographic flow imaging (see, e.g., U.S. Pat. No. 5,485,743), and/or for phase velocity measurement based on Doppler sensing (see, e.g., GB Patent No. 2 359 435 and U.S. Pat. No. 7,712,380) or cross-correlation measurements (see, e.g., U.S. Pat. No. 7,908,930). RF/microwave reflection probe and/or transmission antennas have also been used for measuring water conductivity of multiphase flows (see, e.g., U.S. Pat. No. 6,831,470). Electromagnetic systems have also been used to investigate investigate formation-fluids, such as described in European patent/patent application EP 2 015 109. An apparatus for determining a property of a downhole formation may comprise an array having a plurality of transmitters and receivers capable of propagating electromagnetic waves through the formation. Furthermore, electromagnetic investigation systems may be used to investigate properties of a solid phase contained in or being carried in a liquid/fluid phase. The content of the patents referenced above are incorporated by reference herein for all purposes.

SUMMARY

In one embodiment of the present disclosure, an electromagnetic measurement system for measuring a property of a fluid flowing in a conduit, such as for example a borehole, a pipeline, a pipe, a conduit and/or the like, a fluid contained in an earth formation and/or properties of a solid contained in a fluid is provided. In the embodiment, a metamaterial is used to act as a lens and focus electromagnetic energy into the fluid so that properties of the fluid can be determined. In aspects of the present invention, a metamaterial lens provides for electromagnetic investigation into/inside the fluid/fluid flow. The fluid/fluid flow may be a multiphase mixture and the metamaterial electromagnetic investigation system may be used to obtain properties of the multiphase flow, the phases of the multiphase flow, components of the phases of the multiphase flow and/or the like. In embodiments of the present invention, the metamaterial may comprise a material with a negative refractive index. In some aspects of the present invention, the magnitude of the refractive index of the metamaterial may be matched with a magnitude of the fluid being investigated.

In one embodiment of the present disclosure, a method for enhancing sensing properties of an electromagnetic system for investigating properties of a fluid in a conduit, borehole, pipe, and/or the like is provided, where a metamaterial is used to increase the investigation depth and/or increase the sensitivity of the electromagnetic system.

BRIEF DESCRIPTION OF THE DRAWINGS

The present disclosure is described in conjunction with the appended figures.

Figure 1:
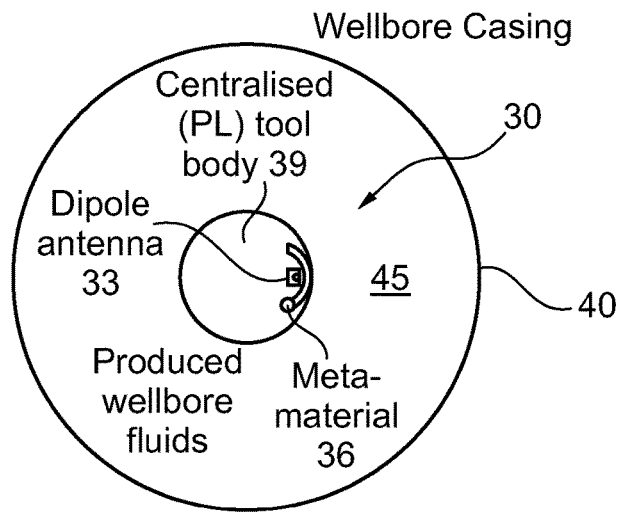
FIG. 1 illustrates an electromagnetic system, comprising a dipole antenna and a metamaterial lens, for investigating a fluid, in accordance with an embodiment of the present invention.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

A metamaterial is defined as a macroscopic composite of periodic or non-periodic structure, whose function is due to both the cellular architecture and chemical composition. Metamaterials may have a designed, non-naturally occurring, response to radiofrequency ("RF") and microwave electromagnetic fields, among other fields. A metamaterial element or lens may be perfect/advantageous in the sense that it manipulates the near field and leads to resolution that is not limited by diffraction. For example, a slab of material with a refractive index having a value of approximately minus one (−1) in air (i.e., a refractive index=1) will focus electromagnetic radiation from a source (S) to an image (I). In such a configuration, metamaterial elements/lenses with sub-wavelength thickness lenses can be used to focus RF and microwave electromagnetic radiation into a fluid.

Certain embodiments of the present invention concern the modification of an electromagnetic field distribution for the purpose of enhancing the range of sensitivity of multiphase metering systems that use electromagnetic ("EM") energy to investigate a fluid. For purposes of this specification, the terms multiphase metering system, fluid sensor, flow sensor, multiphase flowmeter ("MPFM") and the like may be used to describe a sensor system that uses EM energy to investigate/measure properties of a fluid, where the fluid may be contained in a wellbore, a pipe, a pipeline, a conduits and/or the like.

In EM fluid investigation/measurement, such as multiphase flow measuring systems, at sufficiently high RF/microwave frequencies, the measured response of transmission or reflection (or scattering) relates directly or indirectly to the complex permittivity (equivalently the relative permittivity and conductivity) of the multiphase fluid within its sensitivity-zone coverage or depth of investigation. Given that water has a permittivity of about 80, oil about 2.2 and gas about 1, and water has a conductivity of as high as 100 S/m, oil about zero and gas zero, the measurement is primarily sensitive to the water fraction and water conductivity. Dielectric properties of water and oil typically exhibit multiple relaxations that originate from many sources. At low frequencies interfacial effects are particularly prominent and can make interpretation of the dielectric signals problematic. Nevertheless, low frequency signals have the greatest depth of penetration. At higher frequencies, the confounding effects of interface polarization disappear from the signal and the interpretation of the dielectric response in terms of phase fraction is significantly simplified. However, at high frequencies the depth of penetration of the radiation is significantly less and thus the RF/microwave sensing system may only measure/investigate a portion of the fluid in the vicinity of/appurtenant to the sensing system/antennae transmitting the EM radiation into the fluid.

In certain aspects, each transmitter/receiver antenna in an RF/microwave sensing system could be considered as a close approximation to an ideal dipole. As such, the radiation field from the transmitter/receiver antenna will fall as $1/r^3$, with r the radial distance from the antenna. For a system with a plurality of antennas mounted around a pipe periphery (such as in a tomography system, for example as disclosed in U.S. Pat. No. 5,485,743, or a two-transmitter two-receiver compensated differential measurement system as disclosed in U.S. Patent Pub. No. 20110267074) the depth of penetration of the field is determined by a combination of the separation of the transmitter(s) and receiver(s) and by the signal strength compared to the instrument noise floor, which is frequency dependent.

Typically, the highest frequency of the RF/microwave flow measurement system is of the order of 1 to 10 Giga-Hertz ("GHz"). At these types of frequencies the depth of investigation is low at high bulk-conductivity (at high water-cut, at high salinity and/or high temperature). As such, in a wellbore or pipe containing a flow exhibiting significant water fraction, it is often not possible to use EM radiation to probe the entire wellbore/pipe cross-section.

In embodiments of the present invention, metamaterials are used to extend the sensitivity reach of the EM system, particularly at higher frequencies, where the effects of interface polarization disappear. By contrast, simply increasing the transmission power will not solve the problem of depth of investigation since the ratio of reduction in signal with distance will remain the same. In any case the power available is in practice limited and for surface/subsea applications in the hydrocarbon industry, a low-power requirement is advantageous in terms of system competitive advantage and easiness to achieve intrinsic safety.

Metamaterials are, in the broadest sense, materials with properties that are not naturally occurring. Herein, the term metamaterial is, in general, used to refer to a class of materials having negative refractive index and/or that are left-handed or doubly negative materials. In addition, in some aspects of the present invention, materials with spatially designed permittivity may also be used in a MPFM. The former materials are characterized by having both a negative relative permittivity and negative relative permeability.

In an embodiment of the present invention, metamaterials may be created using an array of resonators whose permittivity and permeability go negative at resonance, and providing that the size of resonators size is much less than a wavelength of the EM to be used in the MPFM. In such a configuration, a material with the appropriate average properties can be made. The latter materials, the materials with spatially designed permittivity, are simpler to make, are broadband, but do not exhibit the "perfect lensing" achievable with left handed materials. Nevertheless low profile lenses can be made from the materials with spatially designed permittivity, and these are the RF equivalent of gradient lenses. In addition to these materials, in some embodiments, combined right hand and left hand properties can be designed into strip-line waveguide antennae, which can be designed to have a directional capability.

In one embodiment, a negative refractive index material/lens may be used to manipulate the near field of an EM flow sensor to obtain a "perfect" lens, i.e. a lens that is not constrained by the diffraction limit. In some embodiments, an EM flow sensor comprises a lens of dimension significantly less than a wavelength of the propagating EM energy.

In one embodiment, a cylindrical lens of a metamaterial is disposed insert between the transmitter/receiver antenna (s) of an RF/microwave flow sensing system and the fluid being investigated in a wellbore, pipelines, conduits and/or the like so as to focus the emitted EM radiation from the antenna to a plane along or across the wellbore, pipe or conduit axis. Thus, in such embodiments, instead of a $1/r^3$ falloff in field strength, as found in previous EM fluid sensors, a $1/r^2$ falloff is provided, which provides a significant difference with respect to sensitivity/depth of investigation. In general, this type of falloff is valid for $r>>a$, where a is the length of the dipole. Using such a lens, in embodiments of the present invention, significant enhancements in the penetration depth for a given power output are produced for the EM fluid sensing system.

To provide a conventional lens for the RF frequencies used in fluid sensing would require a lens of significant size, i.e. significantly larger than the wellbore or pipe diameter in which the fluid is contained. However, in embodiments of the present invention, negative refractive index materials are used for the lenses, which have dimensions that are a fraction of a wavelength of the EM energy that is being transmitted in the propagation direction. This allows for design of focused EM flow sensors that can be used within commonly used pipelines and wellbores.

FIG. 1, illustrates an electromagnetic system, comprising a dipole antenna and a metamaterial lens, for investigating a fluid, in accordance with an embodiment of the present invention. The electromagnetic system 30 comprises a dipole antenna 33 and a metamaterial 36. For ease of visualization etc. the power source for the system and other mechanics are not shown. The electromagnetic system 30 is disposed on a tool body 39 that is positioned within a conduit 40, which may comprise a wellbore casing, pipeline, pipe and/or the like. A fluid 45 is contained within the conduit 40 and investigated by the electromagnetic system 30. The fluid 45 may comprise a multiphase mixture, hydrocarbons, production fluids from a wellbore and/or the like.

FIGS. 2(a)-(d) illustrate field distributions produced in a conduit, determined by modeling, for a non-metamaterial focused electromagnetic system and the meta-material focused system described in FIG. 1. In FIG. 2, to demonstrate operation of an embodiment of the present invention, the multiphase fluid was modeled as having a permittivity of 8 (e.g. such as would be found for an oil-continuous oil/water mixture with water-cut ~40%), the tool body was modeled as having permittivity 3 (e.g. a ceramic material) and the metamaterial had a relative permeability $\mu_r=-2.2+0.001i$ and a permittivity $\varepsilon_r=-2.2+0.001i$. Thus the effective refractive index of the metamaterial is $n=-2.2$. FIG. 2 shows the resulting calculations of field distribution for a frequency of 4 GHz.

Figure 2:
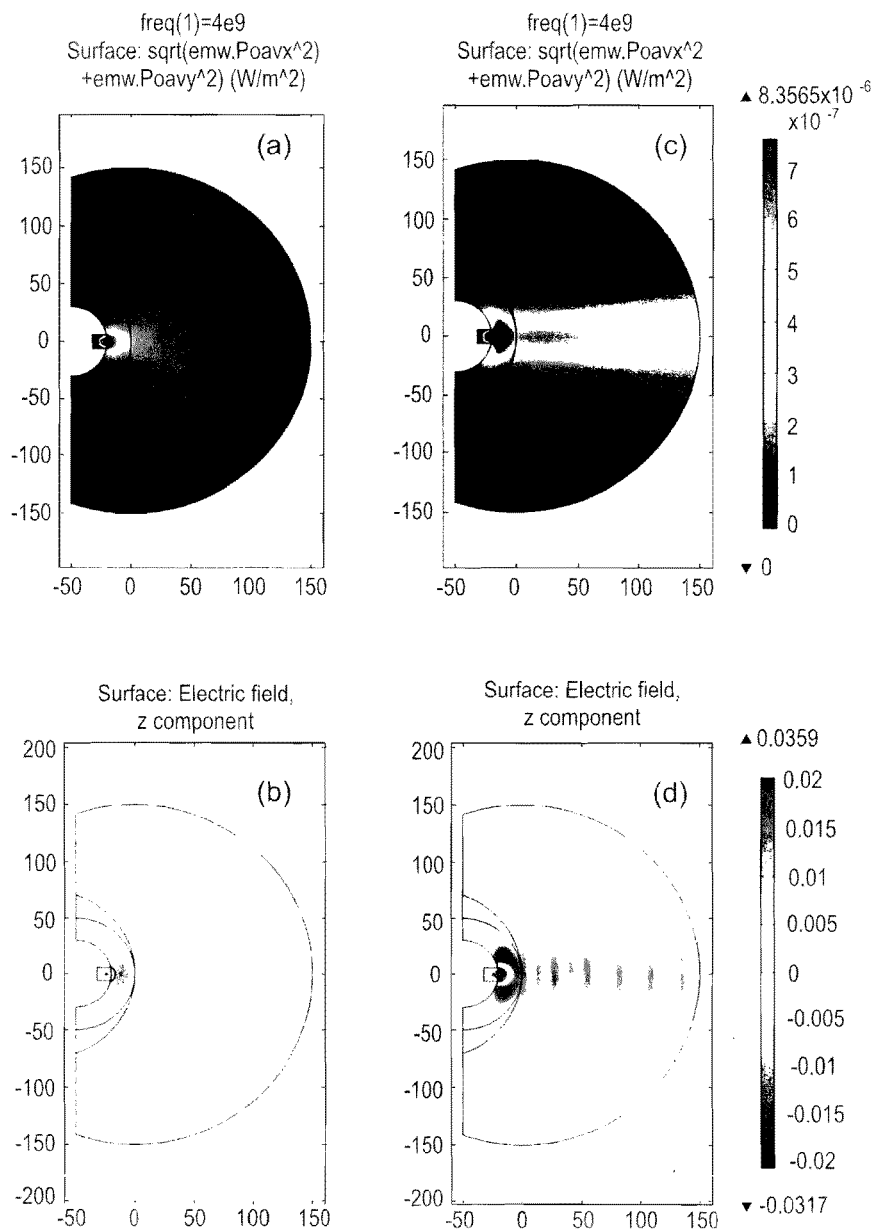
FIGS. 2(a)-(d) illustrate field distributions produced in a conduit, determined by modeling, for a non-metamaterial focused electromagnetic system and the meta-material focused system described in FIG. 1.

In FIG. 2, calculations of a 2D field in a plane perpendicular to the conduit and for a frequency of 4 GHz are shown. In FIGS. 2(a) and (b) instead of a metamaterial layer/lens, the field is modeled for the electromagnetic system of FIG. 1 in which the metamaterial lens is replaced with a material having relative permittivity=3. FIGS. 2(c) and (d) show modeling of the field distribution form the electromagnetic system of FIG. 1 using the metamaterial layer/lens. FIGS. 2(a) and (c) are plots (on the same scale) of time averaged power flow. FIGS. 2(b) and (d) are for the electric field Ez (also with the same scale). The spatial scale is in millimeters (mm).

In FIG. 2(a) the time averaged power flux is plotted and in FIG. 2(b), $E_z$ from the same calculation is plotted. In FIG. 2(a), the expected dipole field, modified by proximity to a conductive plane, is illustrated. In FIGS. 2(c) and 2(d) a metamaterial is introduced and a very clear focusing effect is observed.

Figure 3:
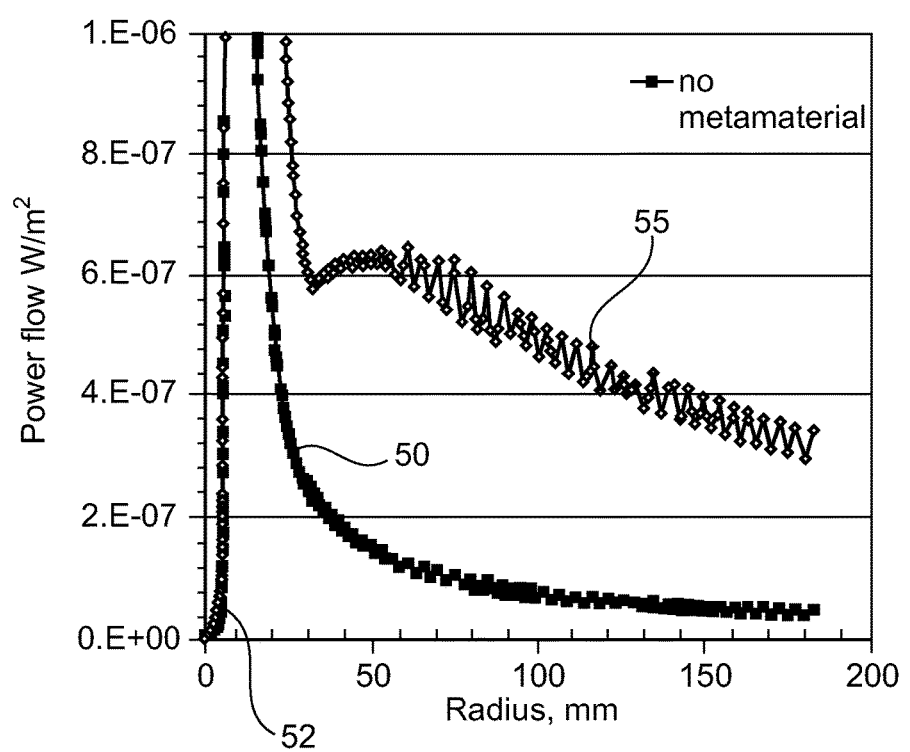
FIG. 3 illustrates how power dissipates, in a direction normal to a conduit, with radius for the electromagnetic system of FIG. 1 when the system comprises a regular material and a metamaterial, in accordance with an embodiment of the present invention.

FIG. 3 illustrates how power dissipates, in a direction normal to a conduit, with radius for the electromagnetic system of FIG. 1 when the system comprises a regular material and a metamaterial, in accordance with an embodiment of the present invention. Curve 50 shows the power flow against radius for the electromagnetic system of FIG. 1 comprising a regular material coupled with the dipole antenna and curve 55 shows the power flow against radius for the electromagnetic system of FIG. 1 comprising a metamaterial lens. Curve 52 shows the power flow against radius for both the electromagnetic system with and without the metamaterial lens, since at these distances from the dipole antenna the power flows overlap.

Whilst the modeling/calculations are provided to illustrate effects of embodiments of the present invention, it is understood that the metamaterial layer, by virtue of being a resonant layer, may only effectively "lens"/focus one or a small range of frequencies. Also, the metamaterial layer can be designed in aspects of the present invention to affect one polarization at a time. Thus, with a single layer, in aspects of the present invention, the metamaterial lens may be configured to affect, focus, for example, a 1 GHz longitudinal signal only. In certain embodiments, designing multiple layers and/or multiple components within one layer provides that the RF/microwave flow sensing system can independently affect/address different frequencies and/or polarizations. As such, in some embodiments, the RF/microwave flow sensing system can be tuned to focus different frequencies/polarizations differently to produce an output that may be tuned to the wellbore/pipe and/or the fluid therein.

Figure 4:
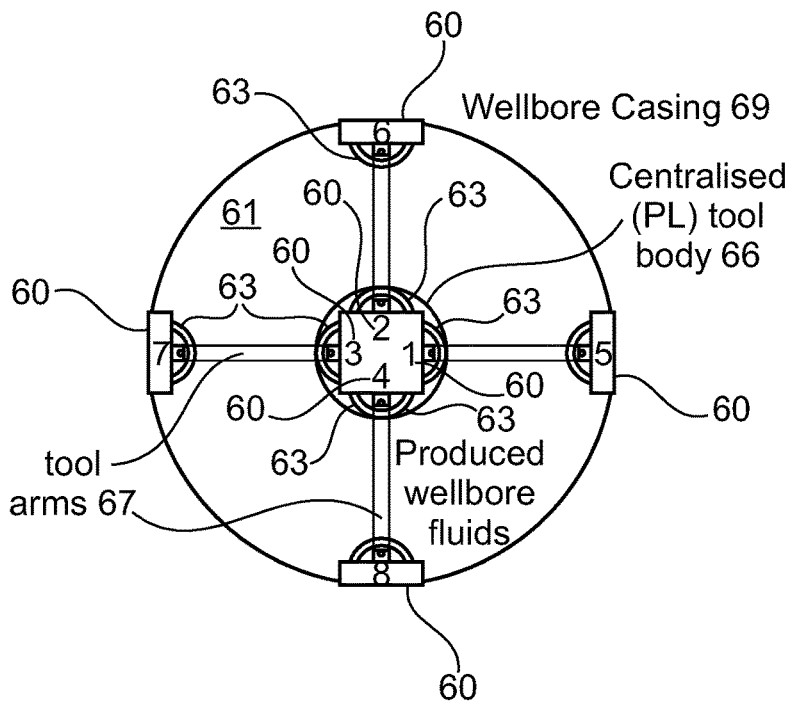
FIG. 4 illustrates an electromagnetic system comprising a metamaterial element for investigating a fluid in a conduit, in accordance with an embodiment of the present invention.

FIG. 4 illustrates an electromagnetic system comprising a metamaterial element for investigating a fluid in a conduit, in accordance with an embodiment of the present invention. As illustrated in FIG. 4, the electromagnetic system comprises, in one embodiment of the present invention, a plurality of dipole antennas 60 coupled with metamaterial layer(s) 63. The minimum number of the dipole antennas 60 in the system being a single pair of the dipole antennas 60 or a single dipole antennas 60 in the case that each antenna acts as a transceiver—transmitting and receiving on its own. The dipole antennas 60 can be arranged around a tool body 66 (e.g. antenna numbers 1 to 4) and/or at the ends of operable arms 67 (e.g. antenna number 5 to 6) to map out the permittivity distribution of a fluid 61 in a conduit 69 over the same and or different cross section(s) of the conduit 69.

The tool body 66 and the operable arms 67 may be part of a tool for introducing the electromagnetic system into the conduit 69. In other embodiments, the electromagnetic system may be coupled with a wall of the conduit to investigate the fluid 61 and/or may investigate the fluid 61 through windows or the like in conduit 69.

In an embodiment of the present invention, a plurality of EM transmission/reflection measurements are made (the minimum number of measurements being one, the measurement being made between one transmitter and one receiver or made by a single antenna acting as a transceiver, i.e., an antenna that acts as both a transmitter and a receiver). In the exemplary figure, FIG. 4, transmission measurements between antennas 1-5, 2-6, 3-7 and 4-8 may be made to map the fluid permittivity across radiuses at different azimuthal angles. Other EM transmission measurement combinations are possible, such as those between antennas 5-6, 6-7, 7-8 and 8-5 to map the fluid permittivity near the casing-wall regions. Near-field measurements 1-2, 2-3, 3-4 and 4-1 could also be made to map the flow permittivity near the wellbore central region. In certain aspects, each depth-of-investigation enhanced antenna (such as antennas number 1-8 in FIG. 4) may act as a transceiver to map out, by reflection measurement the permittivity (phase fraction) of the fluid mixture in its sensitivity path. In certain aspects, each depth-of-investigation enhanced antenna may act as a Doppler sensing transceiver and may map out by reflection/scattering measurements, the velocity of fluid in its sensitivity path. The depth of investigation of transmitting/receiving/transceiver antenna may be variable and/or steerable by using different metamaterial layers and/or components.

Figure 5:
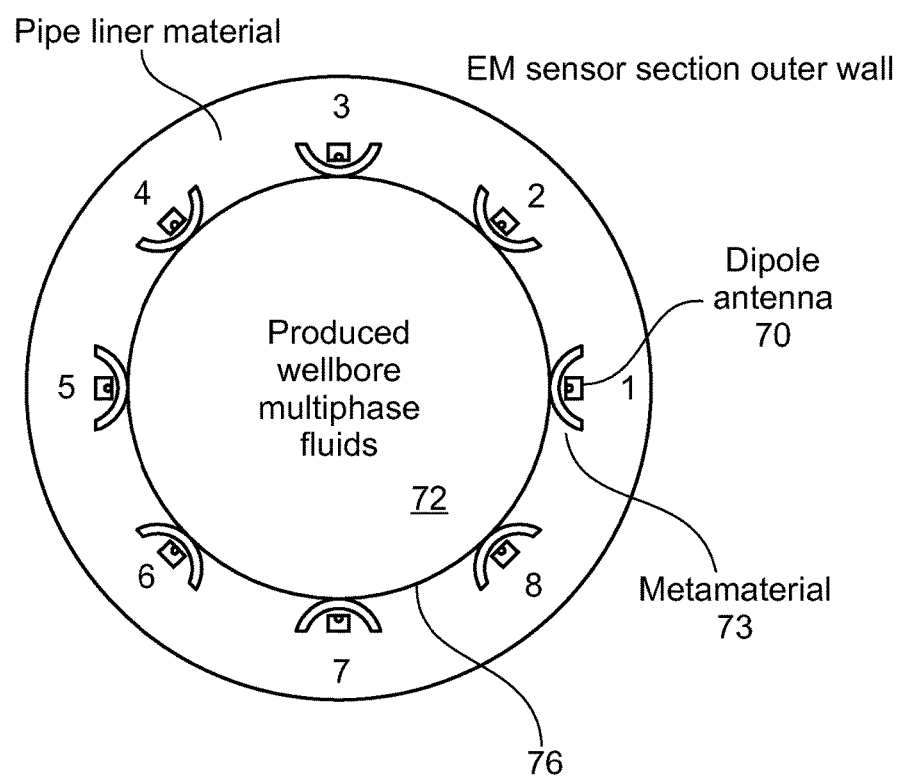
FIG. 5 illustrates an electromagnetic system for investigating properties of a fluid in a conduit using a metamaterial element, in accordance with an embodiment of the present invention.

FIG. 5 illustrates an electromagnetic system for investigating properties of a fluid in a conduit using a metamaterial element, in accordance with an embodiment of the present invention. The electromagnetic system depicted comprises a plurality of dipole antennas 70 (merely by way of example, such as the eight depicted antennas in the figure) with metamaterial layer(s) 73 arranged around a peripheral wall 76 of a conduit containing a fluid 72. The conduit may comprise a pipe, pipeline, a wellbore completion (as part of a downhole permanent flow meter), a topside pipe section (surface/subsea) in which multiphase mixture is flowed and/or the like.

In embodiments of the present invention, for downhole permanent and/or topside permanent/periodic multiphase flow measurements, as illustrated in FIG. 5, a plurality of dipole antennas (merely by way of example, such as the eight depicted antennas in the figure) with metamaterial layer(s) can be arranged around the peripheral of a wellbore completion as part of a downhole permanent flow meter, or around the peripheral of pipe section as part of a topside (surface/subsea) multiphase flow meter. In embodiments of the present invention, improved tomographic measurement of flow-mixture permittivity distribution (hence that of phase fractions), especially around the pipe central region, can be made by the use of antennas with sensing-depth enhancing metamaterial. As with other electrical tomography system, a plurality of EM transmission/reflection measurements could be made, such as (for an 8-antenna system) the transmission measurements between antennas 1-2, 2-3, 3-4, . . . , 7-8; 1-3, 2-4, 3-5, 4-6, 6-8, . . . , 1-5, 2-6, 3-7, 4-8. Compensated differential measurement protocol (single or a plurality of 2-Tx/2-Rx combinations) can be used to improve further short- and long-term stability of the measurement system, for example as disclosed in U.S. Patent Pub. No. 20110267074.

In other embodiments, EM antennas with sensing-depth enhancing or sensing-resolution (smaller than the wavelength) enhancing and steerable metamaterial layer(s) and/or components can be used to sense/measure reflection properties of a fluid in a wellbore/pipe, flow-velocity from Doppler transceiver antenna(s) measurements and/or the like. In one embodiment, a single or plurality of variable sensing-depth and/or variable sensing-direction Doppler transceiver antennas with metamaterial layer(s) may be deployed to map out flow velocity profile(s) at different depths/directions, and/or over a wide range of fluid conductivities (hence over a wide range of water cuts, salinities and temperatures) of a fluid flowing in a wellbore/pipeline.

In certain aspects of the present invention, sensing-resolution enhanced antenna(s), for instance, enable the measurement of wet-gas flow liquid-film thickness smaller than the wavelength of the EM energy used for the sensing. In some embodiments, the antenna(s) may be mounted in the same and/or different cross sections of a borehole or a pipe. In such embodiments, transmission/reflection/Doppler/resonance measurements may be made in the same and/or different cross sections of the borehole or the pipe, including cross-correlation measurements for transit-time (flow velocity) and tomography imaging in 3D of the fluid in the pipe or wellbore.

In some embodiments, the underlying method of depth of measurement enhancement of this invention may be used with other higher frequency EM measurement techniques, such as those based on millimetre-wave and/or Terahertz frequency measurement techniques, including Terahertz tomography-based methods. Additionally, in some embodiments, the enhanced depth of RF/microwave sensing provided by the metamaterial lensed EM signal may be used for robust mixture permittivity and/or conductivity (phase fraction) measurements and can be used in combination with a gamma-ray or X-ray densitometer, and in combination with a multi-energy gamma-ray or multi-energy X-ray system to determine properties of the fluid in the pipe/wellbore/conduit. In some embodiments, the metamaterial-antenna may be used in combination with a differential-pressure device—such as a Venturi, Venturi tube, Venturi nozzle and/or the like—which may be used to determine flow properties of the fluid.

In one embodiment, the present disclosure provides an electromagnetic measurement tool for measuring a property of a fluid in a pipe, wellbore and/or the like. The electromagnetic measurement tool may include a tool body and an antenna coupled with the tool body and configured for placement adjacent fluid flow. In certain aspects, the antenna may include at least one transmitter configured to transmit electromagnetic energy, at least one receiver configured to receive the electromagnetic energy, and a metamaterial element having a negative refractive index, the metamaterial element focusing the electromagnetic energy into the fluid.

Merely by way of example, in some embodiments, the lens may have a thickness of between about 1 mm and about 30 mm and/or may have a semicircular cross section or configuration having a radius between about 13 cm and about 17 cm. In one embodiment, an absolute value of the refractive index of the metamaterial element may be substantially equivalent to an absolute value of the refractive index of the fluid. The metamaterial element may focus electromagnetic energy based on a polarization of the electromagnetic energy. Merely by way of example, the electromagnetic measurement tool may be a nuclear magnetic resonance scanner, a dipole-antenna-array dielectric scanner, a multiphase flow meter, and/or the like. In some embodiments, the metamaterial element may include an array of resonators sized smaller than the wavelength of a focused electromagnetic wave and the permeability and permittivity of at least one resonator may be negative over a range of frequency.

The system may include a computing device comprising a processor and memory. The computing device may be configured to process a property of the fluid. The system may also include a deployment device configured to deploy one or more elements of the fluid sensor within the fluid being measured. In other embodiments, the sensor may be disposed around the pipe, conduit, wellbore and/or the like and may be in contact with the fluid in the pipe, conduit, wellbore and/or the like and be disposed around or within a wall of the pipe, conduit, wellbore and/or the like. The system may further include an antenna coupled communicatively coupled with the computing device. The antenna may include at least one transmitter configured to transmit one or more frequencies of electromagnetic energy. The antenna may also include at least one receiver configured to receive the electromagnetic energy and to provide information associated with the electromagnetic wave to the computing device to measure the property of the borehole/formation fluid. The antenna may further include a metamaterial element having a negative refractive index that focuses the electromagnetic energy.

In yet another embodiment, the present disclosure provides a method of enhancing a measurement of an electromagnetic measurement tool. The method may include providing an electromagnetic measurement tool having: a transmitter configured to transmit electromagnetic energy, a receiver configured to receive the electromagnetic energy, and a metamaterial element comprising a negative refractive index, the metamaterial element focusing the electromagnetic energy. The method may also include placing the electromagnetic measurement tool adjacent a fluid and transmitting electromagnetic energy via the transmitter. The method may further include receiving the electromagnetic energy with the receiver to measure a property of the solid body/rock formation containing a fluid or a fluid.

In some embodiments, the metamaterial element may focus electromagnetic energy in a range between about 20 MHz and about 50 GHz. In another embodiment, the metamaterial element may focus electromagnetic energy in the range between about 20 MHz and about 4 GHz. In some embodiments, the negative refractive index may be a value between about −1 and about −20. In another embodiment, the negative refractive index may be a value between about −1 and about −4. The metamaterial element may focus electromagnetic energy based on a polarization of the electromagnetic energy. In one embodiment, the metamaterial element focuses electromagnetic energy transmitted within a first frequency range and the method additionally includes positioning an additional metamaterial element atop the transmitter, the additional metamaterial element focusing electromagnetic energy transmitted within a second frequency range different than the first frequency range.

Embodiments of the present invention may use properties of dielectrics to focus an electromagnetic signal from a transmitter into the fluid being measured. Dielectric properties typically exhibit multiple relaxations that may originate from several sources. When energy is transmitted at low frequencies from the transmitters, interfacial polarization effects may be prominent and may make interpretation of the dielectric signals problematic. Transmitting at low frequencies, however, may provide an increased penetration depth of the electromagnetic energy within the fluid. In contrast, transmitting high frequency energy from the transmitters may reduce the effects of interfacial polarization and may thus, simplify the interpretation of the dielectric response. Transmitting at high frequencies, however, may reduce the penetration depth of the electromagnetic energy so that the measurement is mainly or substantially confined to outer layers/portions of the fluid being investigated. In other words, the higher the transmitted frequency, the simpler the interpretation while the lower the transmitted frequency, the greater the depth of penetration. Thus, there is often a tradeoff between: (i) measuring at a sufficiently high frequency so that interfacial polarization effects are minimized and the dielectric measurement are easily interpreted in terms of important parameters, and (ii) depth of transmission or penetration of the electromagnetic energy.

Further, in some configurations, the transmitter used for fluid investigation/measurement may closely approximate an ideal dipole. As such the radiation field strength of the transmitted electromagnetic energy in the near field (i.e. within a few wavelengths of the antenna; at 1 GHz, wavelength in fresh water will be approx. 3 cm) may decline by a third power of the radius from the respective transmitter (e.g., the near field radiation strength is inversely proportional to the third power of the radius ($1/r^3$), where r represents the radial distance from the respective dipole transmitter). The sharp decline in the near field radiation strength may limit the power that may be supplied to increase a penetration depth of the electromagnetic energy. Thus, a mere increase in power may not be sufficient to increase a penetration or transmission depth of the electromagnetic energy. Rather, the penetration depth of the electromagnetic energy may be enhanced via more efficient utilization of the available power.

The radiation field strength of the transmitted electromagnetic energy in the far field (i.e., more than a few wavelengths of the antenna) may decline by a second power of the radius from the respective transmitter (e.g., $1/r^2$).

The power intensity at a distance r from an antenna, may be approximated in one dimension by the formula below (Beer's law):

$$I=I_0\exp(-\beta r)\cdot f(r,\theta,\phi)$$

where: $I_0$ represents the power at the antenna, $\exp(-\beta r)$ expresses Beer's law with $\beta$ an absorption coefficient, and $f(r,\theta,\phi)$ the field distribution pattern. For a dipole antenna in near field, $f\propto 1/r^3$, and in far field, $f\propto 1/r^2$. When adding a metamaterial structure, the function $f$ may be modified as shown in the formula below:

$$I=I_0\exp(-\beta r)\cdot\text{meta}(f(r,\theta,\phi))$$

Metamaterials may allow design of the function meta( ) so as to shape the near field in a desired way using optical transformation theory. Depth of penetration of transmitted electromagnetic energy (e.g., electromagnetic waves) into a fluid in a pipe, conduit, wellbore and/or the like may be increased by positioning a lens comprising a metamaterial atop an antenna. The metamaterial lens may be positioned atop transmitters and/or receivers and function as a resonant layer to focus emitted energy and increase a transmission or penetration depth of the emitted energy into the fluid, which thereby enhances the signal received at the receivers and subsequently calculated by a computing device. In some embodiments, non-resonant metamaterials may be used to focus emitted energy and increase a transmission or penetration depth of the emitted energy into the fluid.

The metamaterial lens may include an array of resonators sized smaller than the wavelength of a focused electromagnetic wave and a permeability and permittivity of at least one resonator may be negative at a resonance frequency or within a frequency range so as to focus the electromagnetic wave. The metamaterial lens may focus emitted energy to a plane across the pipe, conduit, wellbore and/or the like and/or may increase the radiation field strength so that the transmitted electromagnetic energy declines by a square of the radius from the respective transmitter instead of by a third power (e.g., radiation field strength may be inversely proportional to the square of the radius ($1/r^2$), where r represents the radial distance from the respective transmitter). Such an increased field strength provides a significant enhancement in the penetration or transmission depth of the electromagnetic energy for a given power output.

The metamaterial lens comprises a negative refractive index which allows the lens to be a small fraction of an emitted electromagnetic wavelength. Merely by way of example, in some embodiments, the negative refractive index value of the metamaterial lens is between about −0.5 and about −6, and more commonly between about between about −1 and about −4. The metamaterial lens may be a "left-handed" or doubly negative material, meaning the material is characterized by having both a negative relative permittivity and negative relative permeability. As described previously, the metamaterial lens may be a synthetic or engineered material including an array of resonators whose permittivity ($\epsilon$) and permeability ($\mu$) go negative at resonance or some defined non-resonant frequency. In some embodiments, the permittivity ($\epsilon$), permeability ($\mu$), and or effective refractive index may be between about −2 and about −20 (and in some embodiments between about −5 and −15), which may match or closely approximate the absolute permittivity of the rock formation, fluid, or structure to be measured and thereby optimize transmission of the electromagnetic energy. In other words, the refractive index of the metamaterial element of an electromagnetic measurement system may numerically match the refractive index of the fluid being investigated (e.g., an average water-fraction flow mixture refractive index being investigated and/or measured; i.e., the absolute values of the indexes may match) so as to minimize an impedance mismatch between the electromagnetic measurement system and the fluid or the formation containing fluid. For example, the metamaterial may be designed to have a refractive index of approximately −10 to numerically match a refractive index of the fluid or formation of approximately +10 (i.e., the absolute value of both indices is approximately 10).

In some embodiments, these resonators are sized less than an emitted wavelength, and in some aspects may be less than 1/10 the emitted wavelength, and configured so that the metamaterial lens includes a desired property. For example, the metamaterial lens may be configured to enhance and/or focus emitted electromagnetic energy within a desired frequency range, such as around 1 GHz (e.g. between about 950 MHz and about 1.05 GHz). As such, electromagnetic energy emitted near 1 GHz would be focused and a depth of transmission or penetration of the electromagnetic energy within the pipe/conduit/borehole increased while electromagnetic energy emitted at lower or higher frequencies remain essentially unaffected. Likewise, the metamaterial lens may be configured to enhance and/or focus electromagnetic energy emitted with a desired polarization (e.g., longitudinal polarization) so that electromagnetic energy emitted with substantially equivalent polarization are focused while electromagnetic energy emitted with other polarizations (e.g., transverse polarization) remain essentially unaffected. In some embodiments, the metamaterial lens includes a combination of polarization and frequency filtering.

Figure 6A:
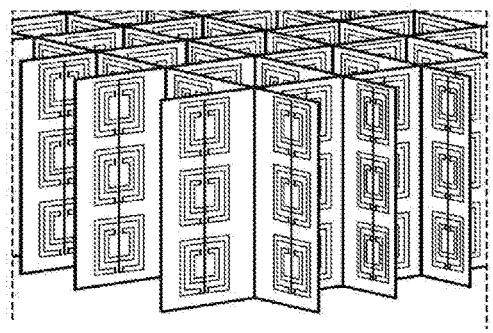
FIGS. 6A-C illustrate examples of metamaterial lenses for use in electromagnetic systems, in accordance with embodiments of the present invention.
Figure 6B:
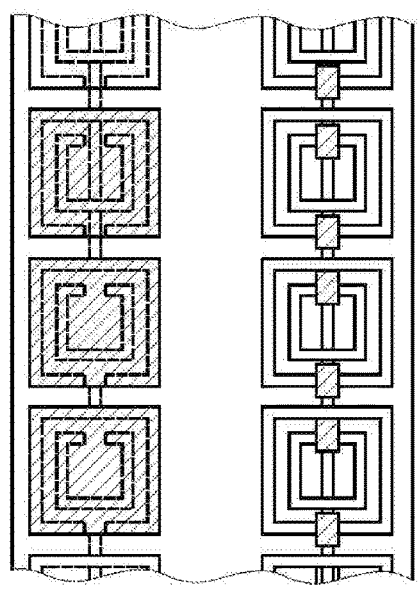
Figure 6C:
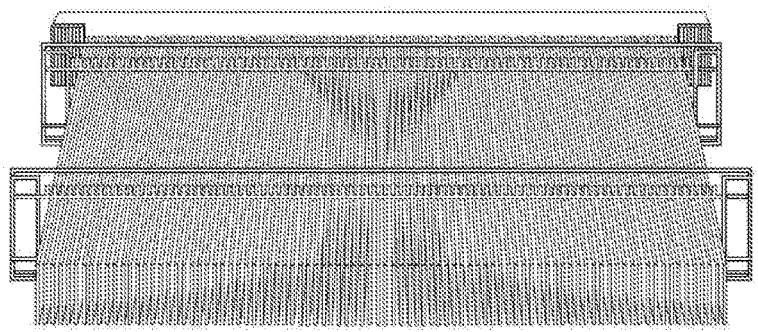

FIGS. 6A-C illustrate examples of metamaterial lenses for use in electromagnetic systems, in accordance with embodiments of the present invention. Metamaterial RF lenses may be constructed from standard metals and dielectrics. Early metamaterial devices were constructed as arrays of wires (negative $\mu$) and split-ring-resonators (negative $\epsilon$). These structures may be fabricated on PCBs (printed circuit board) and assembled into 3D structures. Other structures have been made including "swiss roll" of dielectric and metal, nano rods, loaded waveguides, etc. Examples of such metamaterial lenses are shown in the figures. FIG. 6B illustrates split ring resonators and wires on a sheet and FIGS. 6A & 6C illustrates such sheets of resonators and wires stacked to make a flat lens.

The use of the metamaterial lens having a negative refractive index may allow the near field of the antenna to be manipulated so as to obtain a "perfect" lens, or in other words, a lens that is not constrained by a diffraction limit. The implication is that a lens of dimension significantly less than a wavelength can be constructed, placed atop, disposed adjacent to the antenna, and coupled to/positioned within/proximal to a pipe, conduit, wellbore and/or the like. Further, the metamaterial lens may reduce the size of the effective antennae, provide directional enhancements, and/or the like.

Figure 7:
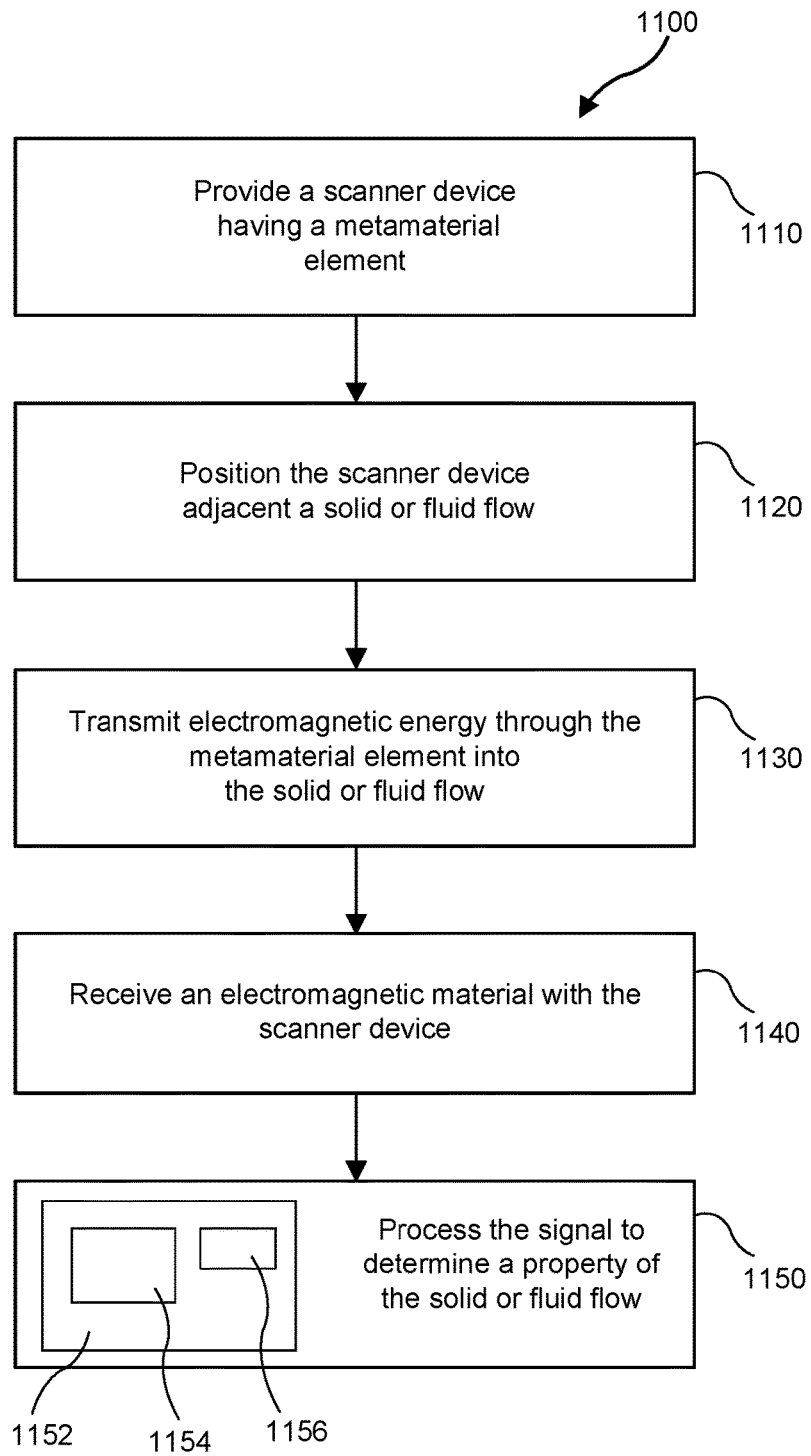
FIG. 7 is a flow-type illustration of a method of using a metamaterial to enhance electromagnetic measurement of properties of a fluid/fluid flow in a conduit.

Referring now to FIG. 7 as provided below, an embodiment of a method 1100 of enhancing a measurement of an electromagnetic measurement system positioned adjacent to a fluid/fluid flow is illustrated.

Method 1100 may describe measurement processes and/or data gathering applications that occur above ground. At block 1110, an electromagnetic measurement system having a metamaterial element or lens, such as those described herein, is provided. At block 1120, the electromagnetic measurement system is positioned adjacent to or in a fluid or fluid flow. The fluid may comprise a wellbore fluid, a multiphase mixture, hydrocarbons and/or the like. The fluid flow may be a fluid flow within a pipe, a suspension within a fluid, a fluid within a rock formation, and/or the like. At block 1130, electromagnetic energy is transmitted through the metamaterial element or lens into the fluid or fluid flow. At block 1140, an electromagnetic signal or energy is received with the electromagnetic measurement system. At block 1150, the electromagnetic signal or energy may be processed to determine one or more properties of the fluid or fluid flow. Processing at block 1150 may be carried out by a computing device 1152 comprising a processor 1154 and memory 1156.

The electromagnetic measurement system may comprise a power source, one or more antennas/transceivers for directing EM radiation into the fluid and receiving EM radiation transmitted through the fluid and/other components.

In the investigation of fluids/fluid flows, the metamaterial properties, the index matching and/or the frequency ranges and/or the like described above, may be used to enhance the electromagnetic investigation of the formation fluid in rock and/or the fluid flow. NMR and/or electromagnetic signals may be focused by the metamaterial lens into the fluid and/or the fluid flow to increase investigation depth. For example, electromagnetic signals may be focused through a pipe or the like or through a window in the pipe to investigate a fluid therein. In other aspects, the electromagnetic measurement system may be disposed within the fluid/fluid flow. In yet other aspects, the fluid/fluid flow may be located within an earth formation and the electromagnetic measurement system may be disposed appurtenant to the earth formation to determine properties of the fluid/fluid flow. Merely by way of example, the electromagnetic measurement system may comprise an NMR system using a metamaterial lens to focus an EM signal into a fluid pipe/conduit/borehole or an earth formation to determine properties of a fluid in pipe/conduit/borehole or in the earth formation.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. An electromagnetic measurement system for measuring a property of a fluid flowing in a pipe or conduit, the system comprising:
    an antenna comprising:
        a plurality of transmitters at respective different positions adjacent to or within the fluid and configured to transmit radio-frequency or microwave electromagnetic energy into the fluid in the pipe or conduit;
        at least one receiver configured to receive electromagnetic energy that has passed through the fluid; and
        a plurality of metamaterial elements having a negative refractive index, each metamaterial element configured as a lens to focus the electromagnetic energy transmitted into the fluid along a plane normal to a longitudinal axis of the pipe or conduit;
    wherein the transmitters and metamaterial elements are arranged around and mounted on a wall of the pipe or conduit, and wherein the pipe or conduit is configured to extract and/or transport fluids extracted from an oilfield.

2. The electromagnetic measurement system of claim 1, wherein the fluid comprises one or more selected from the group consisting of: oil, water, a multiphase fluid, and a gas.

3. The electromagnetic measurement system of claim 1, wherein each metamaterial element comprises a material having a negative relative permittivity and a negative relative permeability over a range of frequencies.

4. The electromagnetic measurement system of claim 1, wherein each metamaterial element comprises a lens positioned on top of the antenna.

5. The electromagnetic measurement system of claim 4, wherein each lens is not positioned over the at least one receiver.

6. The electromagnetic measurement system of claim 4, wherein each metamaterial lens comprises a thickness of between about 1 mm and about 13 mm.

7. The electromagnetic measurement system of claim 4, wherein each metamaterial lens comprises a semicircular cross-sectional configuration having a radius of between about 5 cm and about 10 cm.

8. The electromagnetic measurement system of claim 1, wherein each metamaterial element comprises a coating applied atop the antenna.

9. The electromagnetic measurement system of claim 1, wherein the antenna further comprises a second metamaterial element that focuses electromagnetic energy within a frequency range different than a frequency range of electromagnetic energy focused by the metamaterial elements.

10. The electromagnetic measurement system of claim 1, wherein an absolute value of the refractive index of the metamaterial elements is substantially equivalent to an absolute value of the refractive index of the fluid.

11. The electromagnetic measurement system of claim 1, wherein the antenna is in contact with the fluid or disposed within the fluid.

12. The electromagnetic measurement system of claim 1, wherein the antenna is disposed within the pipe or conduit.

13. The electromagnetic measurement system of claim 1, wherein the property of a fluid comprises a property of a solid contained within the fluid or transported by the fluid.

14. The electromagnetic measurement system of claim 1, wherein the transmitters are configured to transmit electromagnetic energy at a frequency in the range between about 20 MHz and about 50 GHz and the metamaterial elements focus electromagnetic energy at the transmitted frequency.

15. A system for measuring a property of a fluid flowing in a pipe or conduit, the system comprising:
   a computing device comprising a processor and memory, the computing device configured to measure the property of the fluid;
   an antenna comprising:
      a plurality of transmitters at respective different positions adjacent to or within the fluid and configured to transmit radio-frequency or microwave electromagnetic energy into the fluid in the pipe or conduit;
      at least one receiver configured to receive electromagnetic energy after passage through the fluid and to provide information associated with the electromagnetic energy to the computing device to measure the property of the fluid; and
      a plurality of metamaterial elements having a negative refractive index, each metamaterial element configured as a lens to focus the electromagnetic energy transmitted into the fluid along a plane normal to a longitudinal axis of the pipe or conduit;
   wherein the transmitters and metamaterial elements are arranged around and mounted on a wall of the pipe or conduit, and wherein the pipe or conduit is configured for extracting and/or transporting fluids from an oilfield.

16. The system of claim 15, wherein an absolute value of the negative refractive index is matched to an absolute value of the refractive index of the fluid.

17. A method of measuring properties of a fluid flowing within a pipe or conduit, the method comprising:
   providing an electromagnetic measurement system comprising:
      a plurality of transmitters at respective different positions adjacent to or within the fluid and configured to transmit radio-frequency or microwave electromagnetic energy into the fluid in the pipe or conduit;
      at least one receiver configured to receive electromagnetic energy after passage through the fluid; and
      a plurality of metamaterial elements comprising a negative refractive index, each metamaterial element being configured as a lens for focusing the transmitted electromagnetic energy along a plane normal to a longitudinal axis of the pipe or conduit;
   transmitting electromagnetic energy via the transmitters, through the metamaterial elements into the fluid within the pipe or conduit with the metamaterial elements focusing the electromagnetic energy transmitted by the transmitters;
   receiving electromagnetic energy that has passed through the fluid with the at least one receiver; and
   processing properties of the received electromagnetic energy to measure a property of the fluid;
   wherein the transmitters and metamaterial elements are arranged around and mounted on a wall of the pipe or conduit, and wherein the pipe or conduit is configured for extracting and/or transporting fluids from an oilfield.

18. The method of claim 17, wherein the properties of the received electromagnetic energy comprise at least one of an amplitude, a phase and a frequency of the received electromagnetic energy.

19. The method of claim 17, wherein the transmitters are configured to transmit electromagnetic energy at a frequency in the range between about 20 MHz and about 50 GHz and the metamaterial elements focus electromagnetic energy at the transmitted frequency.

20. The method of claim 19, wherein the metamaterial elements focus electromagnetic energy in the range between about 20 MHz and about 4 GHz.

21. The method of claim 17, wherein the negative refractive index comprises a value between about −1 and about −20.

22. The method of claim 17, wherein the negative refractive index comprises a value between about −1 and about −4.

23. The method of claim 17, further comprising configuring the metamaterial elements so that an absolute value of the refractive index of the metamaterial elements is substantially equivalent to an absolute value of the refractive index of the fluid.

24. The method of claim 17, wherein the metamaterial elements focus the electromagnetic energy based on a polarization of the electromagnetic energy.

25. The method of claim 17, wherein each metamaterial element comprises a lens separate from any transmitter and receiver.

26. The method of claim 17, wherein each metamaterial element comprises a metamaterial coating.

27. The method of claim 17, wherein the electromagnetic measurement system comprises a nuclear magnetic resonance scanner, a dipole-antenna dielectric scanner, or a multiphase flow meter.

28. The method of claim 17, wherein the metamaterial element comprises an array of resonators sized smaller than the wavelength of a focused electromagnetic wave, and wherein the permeability and permittivity of at least one resonator is negative at a resonance frequency.

29. The method of claim 17 wherein the pipe or conduit is a surface conduit.

30. An electromagnetic device, being part of a flow measurement system comprising a plurality of transmitter antennas configured to transmit radio-frequency or microwave electromagnetic energy and one or more receivers and/or one or more transceivers, wherein a metamaterial element configured as a lens is inserted between each transmitter and at least one said receiver and/or at least one said transceiver such that the electromagnetic energy is focused by the metamaterial element and there is an enhancement of the signal at the receiver and/or the transceiver, and wherein the transmitter antennas and metamaterial elements are arranged circumferentially around an axis.

31. The electromagnetic device of claim 30, wherein the transmitter antennas contain materials with spatially varying permittivity.

32. The electromagnetic device of claim 30, wherein the transmitter antennas employ waveguides or other materials with right hand and left hand elements.

33. The electromagnetic device of claim 30, wherein the flow measurement system is deployed in a well for the purpose of prospecting for oil, or for injecting substances into an oil field.

34. The electromagnetic device of claim 30, wherein the flow measurement system is deployed in a conduit for extracting and/or transporting fluids from an oil field, for the purpose of monitoring liquid or gas flows within the conduit.

\* \* \* \* \*